US012661074B2

(12) United States Patent
Ishida

(10) Patent No.: US 12,661,074 B2
(45) Date of Patent: Jun. 23, 2026

(54) RADIATION DIAGNOSTIC APPARATUS, RADIATION DETECTOR AND OUTPUT DETERMINATION METHOD

(71) Applicant: CANON KABUSHIKI KAISHA, Tokyo (JP)

(72) Inventor: Akihiro Ishida, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 376 days.

(21) Appl. No.: 18/178,634

(22) Filed: Mar. 6, 2023

(65) Prior Publication Data

US 2023/0293121 A1 Sep. 21, 2023

(30) Foreign Application Priority Data

Mar. 15, 2022 (JP) ................................. 2022-039916
Jan. 19, 2023 (JP) ................................. 2023-006867

(51) Int. Cl.
A61B 6/42 (2024.01)
A61B 6/03 (2006.01)
G06T 12/10 (2026.01)
G06T 19/20 (2011.01)

(52) U.S. Cl.
CPC .............. A61B 6/03 (2013.01); A61B 6/4241 (2013.01); G06T 12/10 (2026.01); G06T 2211/40 (2013.01)

(58) Field of Classification Search
USPC ......... 128/920, 922, 924–925; 382/131–225, 382/254–294; 378/1–90, 205–207, 901; 600/921
See application file for complete search history.

(56) References Cited

U.S. PATENT DOCUMENTS

| | | | | |
|---|---|---|---|---|
| 10,219,775 B2 * | 3/2019 | Nakai | ...................... | A61B 6/50 |
| 10,247,834 B1 | 4/2019 | Shahar et al. | | |
| 2016/0015334 A1 * | 1/2016 | Kobayashi | ............ | G01T 1/2985 |
| | | | | 378/4 |
| 2016/0151035 A1 * | 6/2016 | Noda | ................... | A61B 6/5258 |
| | | | | 378/26 |
| 2018/0177481 A1 * | 6/2018 | Jacob | ...................... | G01T 1/242 |
| 2018/0211417 A1 * | 7/2018 | Miyazaki | ............. | G01N 23/046 |
| 2018/0356543 A1 * | 12/2018 | Shahar | ...................... | G01T 1/36 |
| 2020/0138386 A1 | 5/2020 | Zimmerman et al. | | |
| 2020/0209415 A1 | 7/2020 | Veale | | |

FOREIGN PATENT DOCUMENTS

| | | |
|---|---|---|
| EP | 415 955 A1 | 12/2018 |
| JP | 2020-75078 A | 5/2020 |

OTHER PUBLICATIONS

Extended European Search Report issued on Aug. 2, 2023 in European Patent Application No. 23160308.5, 10 pages.

* cited by examiner

*Primary Examiner* — Marcellus J Augustin
(74) *Attorney, Agent, or Firm* — Oblon, McClelland, Maier & Neustadt, L.L.P.

(57) ABSTRACT

A radiation diagnostic apparatus according to an embodiment includes plural radiation detection elements and a processing circuitry. The radiation detection elements are arranged in a two-dimensional direction. The processing circuitry determines, based on a first output relating to a first detection element included in the radiation elements and a second output relating to a second detection element, an ideal output relating to the first detection element when it is assumed that a surface at which a radiation first arrives on the first detection element is an incident position of the radiation.

11 Claims, 5 Drawing Sheets

RADIATION DIAGNOSTIC APPARATUS, RADIATION DETECTOR AND OUTPUT DETERMINATION METHOD

CROSS-REFERENCE TO RELATED APPLICATIONS

This application is based upon and claims the benefit of priority from Japanese Patent Application No. 2022-039916, filed on Mar. 15, 2022; and Japanese Patent Application No. 2023-006867, filed on Jan. 19, 2023, the entire contents of both of which are incorporated herein by reference.

FIELD

Embodiments described herein relate generally to a radiation diagnostic apparatus, a radiation detector and an output determination method.

BACKGROUND

Conventionally, in an X-ray computed tomography (CT) apparatus, a technique of constructing an arc-faced X-ray detector by arranging, in an arc shape in a fan-angle direction, detection modules in which X-ray conversion elements are arranged in a planar manner has been known. Because such an arc-faced X-ray detector is flat in a cone angle direction, an incident angle of an X-ray with respect to an X-ray conversion detector becomes larger at a position having a larger cone angle.

Generally, as a reconstruction theory for a detected X-ray, it is regarded that an incident position of an X-ray is a position on a surface of an X-ray conversion element at which the X-ray has entered. However, when an X-ray obliquely enters with respect to the surface of an X-ray conversion detector, a position in a depth direction of the X-ray conversion element at which the X-ray is to be absorbed is a probability event and, therefore, not limited to the X-ray conversion element to which the X-ray has entered, the X-ray can be absorbed by the other X-ray conversion detector adjacent thereto. This can deteriorate spatial resolution in a cone angle of an X-ray detector, and can be a factor of reducing an image quality of X-ray image data, such as an image elongated along a body axis direction of a subject.

Therefore, a technique in which a detector module constituted of plural X-ray conversion elements is modularized into small modules, and in which the surface of the X-ray conversion element is directed in an X-ray incident direction in each small module unit has been available. However, in such a structure, scattered radiation arising from the structure of the small module and the like can deteriorate the image quality.

Moreover, an X-ray conversion element used as a direct conversion X-ray detector that directly converts an X-ray by using a semiconductor or a rare gas has a smaller X-ray absorption sectional area compared to indirect conversion detector. Furthermore, thickness of the direct conversion X-ray detector is generally thicker than that of an X-ray conversion element used in an indirect conversion X-ray detector due to a semiconductor crystal acting as a photoelectric conversion element. Because of these reasons, a distance of a path of an X-ray that has obliquely entered in an X-ray conversion element of a direct conversion X-ray detector becomes long, and the direct conversion X-ray detector is apt to be affected by an influence of oblique incidence of an X-ray.

Moreover, in an X-ray flat panel detector (FPD) used for general X-ray photography, all of X-ray conversion elements are arranged on a surface of a large area. Therefore, not only a column direction (cone angle direction), but also a channel direction (fan angle direction) is affected by oblique incidence of an X-ray, and an image quality of X-ray image data can be deteriorated. Furthermore, because penetration of X-ray photon varies according to an energy of the X-ray photon, for example, in a photon counting detector, a degree of influence of oblique incidence of an X-ray varies depending on an energy range projected by an energy bin. Because this causes misalignment of position of the X-ray conversion element projected by the energy bin, an image quality of X-ray image data can be deteriorated.

BRIEF DESCRIPTION OF THE DRAWINGS

FIG. 2 is a diagram illustrating a portion of an X-ray detector on an end portion side of an opening relative to a midplane together with an X-ray that obliquely enters the X-ray detector according to the first embodiment;

FIG. 4 is a diagram illustrating a portion of an X-ray detector on an end portion side of an opening relative to a midplane together with an X-ray that obliquely enters the X-ray detector according to a modification of the first embodiment.

DETAILED DESCRIPTION

Figure 1:
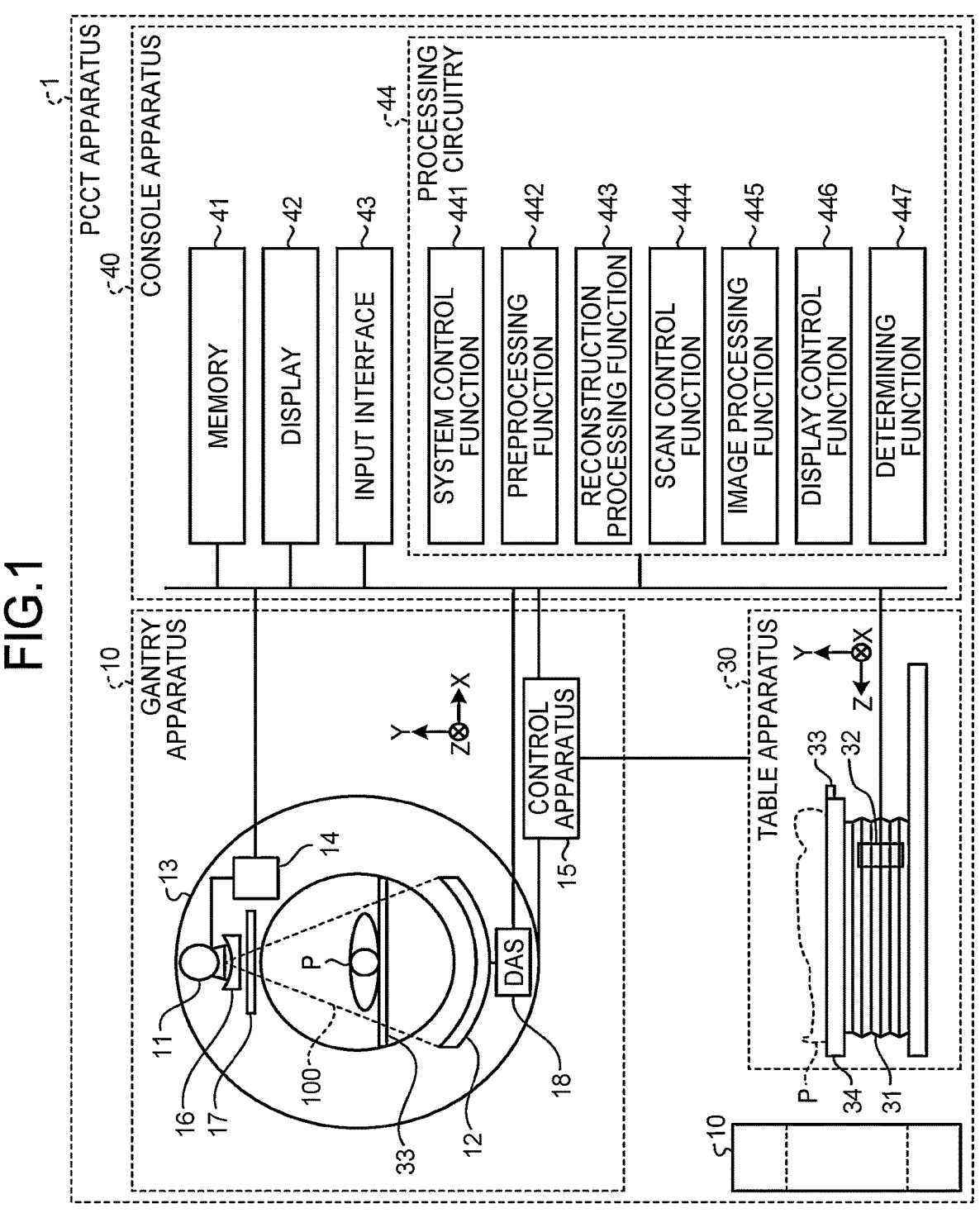
FIG. 1 is a diagram illustrating an example of a configuration of a photon counting CT (PCCT) apparatus 1 according to a first embodiment.

A radiation diagnostic apparatus according to an embodiment includes plural radiation detection elements and a processing circuitry. The radiation detection elements are arranged in a two-dimensional direction. The processing circuitry determines an output corresponding to a reconstruction position of a first detection element based on a first output relating to the first detection element included in the radiation detection elements and a second output relating to a second detection element around the first detection element.

Hereinafter, embodiments of a radiation diagnostic apparatus and a radiation detector will be explained with reference to the drawings. In the following embodiments, components to which common reference signs are assigned are supposed to perform similar actions, and duplicated explanation will be omitted appropriately. The radiation diagnostic apparatus and the radiation detector according to the present application are not limited to the embodiments described below. Moreover, for more specific explanation, radiation according to embodiments is assumed to be X-ray. The radiation according to the embodiments are not limited to X-ray, but may also be other radiation (charged particle or electromagnetic wave according to various wavelengths) and the like.

The radiation detector according to the embodiments includes plural radiation detectors arranged in a two-dimensional direction. The two-dimensional direction is, for example, a cone angle direction and a fan angle direction. The cone angle direction and the fan angle direction will be explained later. In the following, for specific explanation, it is assumed to be a photon counting X-ray detector (hereinafter, denoted as photon counting X-ray detector). The photon counting X-ray detector includes a direct conversion X-ray detector including, for example, a semiconductor element that directly converts an incident X-ray into an electrical signal. The photon counting X-ray detector may include, instead of the direct conversion X-ray detector, an indirect conversion X-ray detector.

The radiation detector according to embodiments are not limited to the photon counting X-ray detector, but may also be an integral-type (also denoted as current-mode measurement type or energy integral type) X-ray detector. The integral-type X-ray detector includes a direct conversion or indirect conversion X-ray detector. For example, the radiation detector may include an X-ray panel flat detector (FPD) used in general X-ray photography as an integral-type X-ray detector.

Moreover, for specific explanation, the radiation diagnostic apparatus according to the embodiments is supposed to be an X-ray computed tomography (CT) apparatus. More specifically, the radiation diagnostic apparatus according to the embodiments will be explained as a photon counting X-ray CT apparatus (hereinafter, denoted as PCCT apparatus) that is capable of performing photon counting CT. The PCCT apparatus is an apparatus that can reconstruct X-ray CT image data of high S/N ratio by counting X-ray beams that have passed through a subject, for example, by using a direct conversion X-ray detector. The radiation diagnostic apparatus according to the embodiments may be an X-ray CT apparatus including an integral-type X-ray detector instead of the photon counting X-ray detector. Moreover, the radiation diagnostic apparatus may be an X-ray diagnostic apparatus including an FPD (for example, X-ray diagnostic apparatus for general radiography, X-ray diagnostic apparatus for circulation organs (angiography), and the like).

First Embodiment

FIG. 1 is a diagram illustrating an example of a configuration of a PCCT apparatus 1 according to a first embodiment. The PCCT apparatus 1 may be referred to as radiographic diagnostic apparatus also. As illustrated in FIG. 1, the PCCT apparatus 1 includes a gantry apparatus 10, a table apparatus 30, and a console apparatus 40. In the present embodiment, a rotation axis of a rotating frame 13 in a non-tilted state or a direction of length of a table top 33 of the table apparatus 30 is defined as a Z-axis direction, an axial direction that is perpendicular to the Z-axis direction and horizontal with respect to a floor surface is defined as an X-axis direction, and an axial direction that is perpendicular to the Z-axis direction and vertical with respect to the floor surface is defined as a Y-axis direction. Although the gantry apparatus 10 is illustrated in plurality in FIG. 1 for explanation's sake, as a component of the PCCT apparatus 1 in actual state, just one apparatus of the gantry apparatus 10 is provided.

The gantry apparatus 10 and the table apparatus 30 operate based on an operation by a user through the console apparatus 40, or on an operation by a user through an operating unit arranged in the table apparatus 30. The gantry apparatus 10, the table apparatus 30, and the console apparatus 40 are wirelessly or wired connected to one another such that mutual communication is possible.

The gantry apparatus 10 is an apparatus that includes an imaging system irradiating an X-ray 100 to a subject P, and collecting detection data of the X-ray 100 that has passed through the subject P. More specifically, the gantry apparatus 10 includes an X-ray tube 11 (X-ray generating unit), a wedge 16, a collimator 17, an X-ray detector 12, an X-ray high-voltage apparatus 14, a data acquisition system (DAS) 18, the rotating frame 13, and a control apparatus 15.

The X-ray tube 11 is a vacuum tube that generates the X-ray 100 by irradiating thermions from a cathode (filament) toward an anode (target) by receiving application of a high voltage from the X-ray high-voltage apparatus 14 and supply of a filament current. The thermions collide against the target to generate the X-ray 100. The X-ray 100 generated at a tube focal spot in the X-ray tube 11 is formed into a cone beam shape, for example, through the collimator 17, to be irradiated to the subject P. For example, the X-ray tube 11 includes a rotating anode X-ray tube that generates an X-ray by irradiating thermions to a rotating anode.

As illustrated in FIG. 1, the X-ray 100 irradiated in a cone beam shape is to have a shape spreading in a fan shape in the X-axis direction. Accordingly, an angle indicating the spread in the X-axis direction of the X-ray 100 irradiated in a cone beam shape is called fan angle. Moreover, an angle indicating the depth in the Z-axis direction of the X-ray 100 irradiated in a cone shape is called cone angle. Therefore, the X-axis direction is also referred to as fan angle direction, and the Z-axis direction is also referred to as cone angle direction.

The X-ray detector 12 detects photons of an X-ray generated by the X-ray tube 11. Specifically, the X-ray detector 12 detects an X-ray that has irradiated from the X-ray tube 11 and passed through the subject P in a photon unit, and outputs an electrical signal corresponding to the amount of X-ray to the DAS 18. The X-ray detector 12 includes plural detection element strings in which plural detection elements (also denoted as X-ray detection elements) are arranged in the fan angle direction (also denoted as channel direction), for example, along one arc about the focal spot of the X-ray tube 11. In the X-ray detector 12, the detection element strings are flatly arranged along the Z-axis direction. That is, the X-ray detector 12 has a structure in which the detection element strings are arranged flatly along the cone angle direction (also denoted as column direction, row direction, and slice direction). The detection elements in the X-ray detector 12 correspond to radiation detection elements in a radiation detector.

The PCCT apparatus 1 includes various types, such as a rotate/rotate-type (third generation CT) in which the X-ray tube 11 and the X-ray detector 12 rotate around the subject P as an integrated unit and a stationary/rotate-type (fourth generation CT) in which many detection elements arrayed in a ring shape are fixed and only the X-ray tube 11 rotates around the subject P, and any type can be applied to the present embodiment.

The X-ray detector 12 is a direction conversion X-ray detector that includes a semiconductor element converting an incident X-ray into an electric charge. The X-ray detector 12 of the present embodiment includes, for example, at least one high voltage electrode, at least one semiconductor crystal, and plural reading electrodes. The semiconductor element is also referred to as X-ray conversion element. The semiconductor crystal is implemented, for example, by CdTe (cadmium telluride), CdZnTe (cadmium Zinc telluride (CZT)), and the like. In the X-ray detector 12, electrodes are arranged on two surfaces opposing to each other about the semiconductor crystal and that are perpendicular to the Y-axis direction. That is, in the X-ray detector 12, plural anode electrodes (also denoted as reading electrode or pixel electrode) and a cathode electrode (also denoted as common electrode) are arranged across the semiconductor crystal. Hereinafter, a surface formed with the cathode electrode is denoted as cathode surface.

Between the reading electrode and the common electrode, a bias voltage is applied. In the X-ray detector 12, when an X-ray is absorbed in the semiconductor crystal, an electron-hole pair is generated, and an electron moves to an anode side (anode electrode (reading electrode) side) and a hole moves to a cathode side (cathode electrode side), and a signal relating to detection of an X-ray is thereby output from the X-ray detector 12 to the DAS 18.

The rotating frame 13 supports the X-ray tube 11 and the X-ray detector 12 rotatably about a rotation axis. Specifically, the rotating frame 13 supports the X-ray tube 11 and the X-ray detector 12 so as to oppose to each other. The rotating frame 13 is a ring-shaped frame that rotates the X-ray tube 11 and the X-ray detector 12 by the control apparatus 15 described later. The rotating frame 13 is rotatably supported by a fixing frame that is made from metal, such as aluminum. The rotating frame 13 rotates at a uniform angular speed about the rotation axis, receiving a power from a driving mechanism of the control apparatus 15.

The rotating frame 13 further supports the X-ray high-voltage apparatus 14 and the DAS 18 in addition to the X-ray tube 11 and the X-ray detector 12. The rotating frame 13 as described is housed in a substantially cylindrical casing in which an opening (bore) providing imaging space is formed. A center axis of the opening coincides with a rotation axis of the rotating frame 13.

The X-ray high-voltage apparatus 14 includes a high-voltage generator that has an electric circuitry, such as a transformer and a rectifier, and that has a function of generating a high voltage to be applied to the X-ray tube 11 and a filament current to be supplied to the X-ray tube 11, and an X-ray control apparatus that controls an output voltage according to an X-ray to be irradiated by the X-ray tube 11. The high-voltage generator may be of transformer type, or may be inverter type. The X-ray high-voltage apparatus 14 may be arranged in the rotating frame 13, or on a fixing frame (not illustrated) of the gantry apparatus 10. The fixing frame is a frame that rotatably supports the rotating frame 13.

The control apparatus 15 includes a processing circuitry including a central processing unit (CPU) and the like, and a driving mechanism, such as motor and actuator. The processing circuitry includes a processor, such as a CPU and a micro processing unit (MPU), as a hardware resource, and a memory, such as a read only memory (ROM) and a random access memory (RAM). Moreover, the control apparatus 15 may be implemented by a processor, such as a graphics processing unit (GPU), an application specific integrated circuit (ASIC), a programmable logic device (for example, simple programmable logic device (SPLD), complex programmable logic device (CPLD)), and a field programmable gate array (FPGA).

When the processor is, for example, CPU, the processor implements a function by reading and executing a program stored in a memory. On the other hand, when the processor is ASIC, instead of storing a program in a memory, a relevant function is directly installed as a logic circuitry in a circuitry of the processor. Respective processors of the present embodiment are not limited to be configured as a single unit of circuitry per processor, but may be composed of plural independent units of circuitry combined as a single circuitry to implement the function. Furthermore, it may be configured to implement the function by integrating plural component elements in one processor.

Moreover, the control apparatus 15 has a function of controlling operation of the gantry apparatus 10 and the table apparatus 30 by receiving an input signal from an input interface 43 attached to the console apparatus 40 or the gantry apparatus 10. For example, the control apparatus 15 performs control of rotating the rotating frame 13, control of tilting the gantry apparatus 10, and control of operating the table apparatus 30 and the table top 33 by receiving an input signal. The control of tilting the gantry apparatus 10 may be implemented by rotating the rotating frame 13 about an axis parallel to the X-axis direction by the control apparatus 15 based on an inclination angle (tilt angle) information input by the input interface 43 attached to the gantry apparatus 10. Moreover, the control apparatus 15 may be arranged in the gantry apparatus 10, or may be arranged in the console apparatus 40.

The wedge 16 is a filter to adjust an X-ray dose of the X-ray 100 irradiated from the X-ray tube 11. Specifically, the wedge 16 is a filter to attenuate the X-ray 100 irradiated from the X-ray tube 11 such that the X-ray 100 to be irradiated to the subject P has a predetermined distribution by letting it pass therethrough. The wedge 16 is, for example, a wedge filter or a bow-tie filter, and is a filter formed by processing aluminum so as to have a predetermined target angle and predetermined thickness.

The collimator 17 is a lead plate to narrow the X-ray 100 that has passed through the wedge 16 into an X-ray irradiation range, and forms a slit by combination of plural lead plates and the like.

The DAS 18 has plural units of counting circuitry. Each unit of the counting circuitry includes an amplifier that performs amplification processing with respect to an electrical signal output from each detection element of the X-ray detector 12, and an A/D convertor that converts the amplified electrical signal into a digital signal, and generates detection data, which is a result of counting processing using a detection signal of the X-ray detector 12. The result of counting processing is data to which the number of photons of an X-ray of each energy bin is allocated. The energy bin corresponds to an energy range of a predetermined width. For example, the DAS 18 counts photons (X-ray photons) originated from an X-ray that has irradiated from the X-ray tube 11 and passed through the subject P, and generates a result of the counting processing in which an energy of the counted photons is discriminated as detection data. The DAS 18 is one example of data collecting unit.

The detection data generated by the DAS 18 is transferred to the console apparatus 40. The detection data is a set data of a channel number of a detector pixel of a generation source, a column number, a view number indicating a collected view (also referred to as projection angle), and a value indicating a detected X-ray dose. As the view number, collected order (collection time) of a view may be used, or number (for example, 1 to 1000) indicating a rotation angle of the X-ray tube 11 may be used. The respective units of counting circuitry in the DAS 18 are implemented, for example, by a circuitry group in which circuitry apparatus capable of generating detection data are mounted. In the present embodiment, when simply referring to "detection data", it signifies both pure raw data that is data detected by the X-ray detector 12 before subjected to preprocessing, and raw data that is obtained by subjecting the pure raw data to preprocessing. Note that data before preprocessing (detection data) and data after preprocessing can be denoted as projection data collectively.

The bed apparatus 30 is an apparatus on which the subject P to be scanned is placed and that moves the subject P, and includes a base 31, a table driving apparatus 32, the table top 33, and a table-top supporting frame 34. The base 31 is a casing that supports the table-top supporting frame 34 movably in a vertical direction. The table driving apparatus 32 is a motor or an actuator that moves the table top 33 on which the subject P is placed in a direction of longitudinal axis of the table top 33. The table driving apparatus 32 moves the table top 33 according to control by the console apparatus t 40 or control by the control apparatus 15. The table top 33 arranged on an upper surface of the table-top supporting frame 34 is a plate on which the subject P is placed. The table driving apparatus 32 may move the table-top supporting frame 34 in a direction of the longitudinal axis of the table top 33, in addition to the table top 33.

The console apparatus 40 is a apparatus that performs a control of the gantry apparatus 10, generation of CT image data based on a scan result by the gantry apparatus 10, and the like. The console apparatus 40 includes a memory 41 (storage unit), a display 42 (display unit), the input interface 43 (input unit), and processing circuitry 44 (processing unit). Data communication among the memory 41, the display 42, the input interface 43, and the processing circuitry 44 is performed through a bus.

The memory 41 is implemented, for example, by a semiconductor memory elements, such as a RAM and a flash memory, a hard disk drive (HDD), a solid state drive (SSD), an optical disk, or the like. Moreover, the memory 41 may also be a driving apparatus that reads and writes various kinds of information between a portable storage medium, such as a compact disc (CD), a digital versatile disc (DVD), and a flash memory, and a semiconductor memory, such as a RAM, or the like. The memory 41 stores, for example, projection data and reconstruction image data. Furthermore, a storage area of the memory 41 may be in the PCCT apparatus 1, or may be in an external storage apparatus connected through a network. Moreover, the memory 41 stores a control program according to the present embodiment. Furthermore, the memory 41 is one example of a storage unit.

The display 42 displays various kinds of information. For example, the display 42 outputs a medical image (CT image) generated by the processing circuitry 44, a graphical user interface (GUI) to accept various kinds of operations from an operator, and the like. For example, as the display 42, a liquid crystal display (LCD), an organic electroluminescence display (OELD), a plasma display, or other arbitrary displays can be used appropriately. Moreover, the display 42 may be arranged in the gantry apparatus 10. The display 42 may be of desktop type, or may be configured with a tablet terminal that can communicate with the console apparatus 40 wirelessly, or the like.

The input interface 43 accepts various kinds of input operations from an operator, and converts the accepted input operation into an electrical signal, to output to the processing circuitry 44. For example, the input interface 43 accepts a collection condition when projection data is collected, a reconstruction condition when a CT image is reconstructed, an image processing condition when a post processing image is generated from a CT image, and the like from an operator. As the input interface 43, for example, a mouse, a keyboard, a trackball, a switch, a button, a joystick, a touch pad, a touch panel display, and the like can be appropriately used.

In the present embodiment, the input interface 43 is not limited to ones having a physical operating part, such as a mouse, a keyboard, a trackball, a switch, a button, a joystick, a touchpad, and a touch panel display. For example, a processing circuitry of an electrical signal that receives an electrical signal corresponding to an input operation from an external input apparatus arranged separately from the apparatus, and that outputs this electrical signal to the processing circuitry 44 is also included in examples of the input interface 43. Furthermore, the input interface 43 is one example of input unit. The input interface 43 may be arranged in the gantry apparatus 10. Moreover, the input interface 43 may be configured with a tablet terminal that is capable of wireless communication with the console apparatus 40.

The processing circuitry 44 controls overall operation of the PCCT apparatus 1 according to an electrical signal of an input operation output from the input interface 43. For example, the processing circuitry 44 includes a system control function 441, a preprocessing function 442, a reconstruction processing function 443, a scan control function 444, an image processing function 445, a display control function 446, and a determining function 447. For example, respective processing functions performed by the system control function 441, the preprocessing function 442, the reconstruction processing function 443, the scan control function 444, the image processing function 445, the display control function 446, and the determining function 447, which are components of the processing circuitry 44 illustrated in FIG. 1, are stored in the memory 41 in a form of computer-executable program.

The processing circuitry 44 is, for example, a processor, and reads respective programs from the memory 41, and implements functions corresponding to the read programs by executing the programs. In other words, the processing circuitry 44 that has read the respective programs is to have the respective functions illustrated in the processing circuitry 44 in FIG. 1. The processing circuitry 44 that implements the system control function 441 is one example of a control unit. The processing circuitry 44 that implements the preprocessing function 442 is one example of the preprocessing unit. The processing circuitry 44 that implements the reconstruction processing function 443 is one example of a reconstruction processing unit. The processing circuitry 44 that implements the scan control function 444 is one example of the scan control unit. The processing circuitry 44 that implements the image processing function 445 is one example of the image processing unit. The processing circuitry 44 that implements the display control function 446 is one example of a display control unit. The processing circuitry 44 that implements the determining function 447 is one example of a determining unit. Moreover, the processing circuitry 44 may be one example of the control unit.

Although a case in which the system control function 441, the preprocessing function 442, the reconstruction processing function 443, the scan control function 444, and the display control function 446 are implemented by a single unit of the processing circuitry 44 is illustrated in FIG. 1, embodiments are not limited thereto. For example, the processing circuitry 44 may be configured by combining plural independent processors, and may implement the respective processing functions by executing the respective programs by the respective processors. Furthermore, the respective processing functions included in the processing circuitry 44 may be implemented by a single or plural units of processing circuitry in a distributed or integrated manner.

The processing circuitry 44 controls various kinds of functions of the processing circuitry 44 based on an input operation accepted from the operator through the input interface 43 by using the system control function 441.

The processing circuitry 44 generates data that is obtained by subjecting the ideal detection data determined by the determining function 447 to preprocessing, such as logarithmic conversion processing, offset correction processing, sensitivity correction processing among channels, and beam hardening correction. The ideal detection data will be explained later.

The processing circuitry 44 generates CT image data by performing reconstruction processing using the filtered back-projection method, the successive approximation construction method, or the like with respect to projection data generated by the preprocessing function 442, by using the reconstruction processing function 443.

The processing circuitry 44 acquires two-dimensional positioning image data of the subject P to determine a scan range, an imaging condition, and the like by using the scan control function 444. The positioning image data is also referred to as scanno-image data or scout image data.

The processing circuitry 44 converts the CT image data generated by the reconstruction processing function 443 by a publicly known method into tomography data of an arbitrary section or three-dimensional image data based on an input operation accepted from an operator through the input interface 43 by using the image processing function 445. Generation of three-dimensional image data may be performed by the reconstruction processing function 443 directly.

The processing circuitry 44 causes the display 42 to display the tomography image data and the three-dimensional image data processed by the image processing function 445, by using the display control function 446. Moreover, the display control function 446 causes the display 42 to display various kinds of GUI.

The processing circuitry 44 determines an output corresponding to a reconstruction position of a first detection element based on a first output relating to the first detection element included in plural radiation detection elements (detection elements in the X-ray detector 12), and on a second output relating to a second detection element around the first detection element, by using the determining function 447. The reconstruction position is a position that is used, for example, in calculation of reconstruction based on a determined output, and that indicates a representative point of the first detection element. The reconstruction position is, for example, a surface (cathode surface) at which an X-ray arrives in the first detection element. The reconstruction position is not limited to the cathode surface in the first detection element. For example, it may be an arbitrary position inside the semiconductor crystal on the anode electrode in the first detection element. In the following, for specific explanation, it is supposed that the reconstruction position is an incident position at which an X-ray enters on the cathode surface in the first detection element.

The processing circuitry 44 determines an ideal output relating to the first detection element when it is assumed that a surface at which an X-ray arrives on a surface (cathode surface) in the first detection element is the incident position based on the first output relating to the first detection element included in the detection elements in the X-ray detector 12 and on the second output relating to the second detection element around the first detection element. The incident position of the X-ray is a position at which an X-ray path (also referred to as ray) to the first detection element first hits on a surface of the X-ray detector 12. In other words, the incident position of an X-ray corresponds to, for example, a position at which an X-ray path that has passed through the subject P or a direct beam path not passing through the subject P, not scattered ray of the X-rays, hits on the cathode surface.

The second detection element is, for example, plural detection elements that surround the first detection element, not limited to at least one detection element adjacent to the first detection element. The first output corresponds to detection data (pure raw data or number of counts) relating to the first detection element, and the second output corresponds to detection data (pure raw data or number of counts) relating to the second detection element. When the radiation diagnostic apparatus is X-ray diagnostic apparatus and integral-type X-ray CT apparatus, for example, the first output corresponds to pure raw data output from the first detection element, and the second output corresponds to pure raw data output from the second detection element.

The ideal output corresponds to, in a case in which the X-ray obliquely enters the cathode surface (hereinafter, opposing surface) opposing to the reading electrode (hereinafter, first electrode) of the first detection element, an output relating to the first electrode (for example, number of counts or current value) when an electron generated by an X-ray is read by the first electrode. For example, the opposing surface corresponds to a surface right above the first electrode along the Y-axis direction. Moreover, the second detection element is set in advance according to an incident angle of a ray of an X-ray that obliquely enters the opposing surface. In the PCCT apparatus 1, an output corresponding to the first output and the second output, and the reconstruction position of the first detection element (for example, it may be denoted as ideal output) is the number of counts obtained by counting photons in an X-ray. The ideal output corresponds to the output count obtained by counting, supposing that a position at which an X-ray path to the first detection element first hits on a surface of the X-ray detector 12 is the incident position of the X-ray.

Specifically, the processing circuitry 44 determines an output (ideal output relating to the first detection element) corresponding to a reconstruction position of the first detection element by using a first weight according to a first angle from a reference line to the first detection element and a second weight according to a second angle from the reference line to the second detection element in a direction (for example, the column direction) on a plane including the first detection element and the second detection element out of the two-dimensional direction (the channel direction and the column direction) in which the detection elements are arranged, by using the determining function 447. That is, the determining function 447 calculates an output expected to be statistically originally output by the respective detection elements, that is, likely ideal output by performing weighted calculation by using an output of a detection element around each of the detection elements in each of the detection elements in the X-ray detector 12.

The reference line is, for example, a line connecting a center (midplane) in a cone angle direction in the X-ray detector 12 and the tube focal spot. The first weight and the second weight are set based on a material that converts an X-ray (radiation) into an electron or a visible light in the first detection element and the second detection element, thickness of the material, and an angle at which an X-ray enters the first detection element. For example, in the case of direction conversion X-ray detector, the material is semiconductor crystal. Moreover, in the case of indirect conversion X-ray detector, the material is, for example, scintillator. The angle at which an X-ray enters the first detection element corresponds to the first angle described above. The first weight and the second weight are set in advance by various kinds of simulation (for example, Monte Carlo simulation) using the first angle, thickness of the semiconductor crystal, the material, and the like, or by preliminary calibration test (experiment).

When the direction in the plane including the first detection element and the second detection element is, for example, the cone angle direction (column direction), that is, when the first detection element and the second detection element are arranged along the cone angle direction, the angle from the reference line to the first detection element corresponds to an angle between a straight line connecting the first detection element and the tube focal spot and the reference line (hereinafter, denoted as first cone angle). Moreover, when the direction in the plane including the first detection element and the second detection element is, for example, the cone angle direction (column direction), an angle from the reference line to the second detection element (hereinafter, denoted as second cone angle) corresponds to an angle between a straight line connecting the second detection element and the tube focal spot and the reference line.

That is, when the first detection element and the second detection element are arranged along the cone angle direction, the processing circuitry 44 determines an output (ideal output relating to the first detection element) corresponding to a reconstruction position of the first detection element, for example, by adding up a first multiplication value obtained by multiplying the first output by the first weight and a second multiplication value obtained by multiplying the second output by the second weight by using the first weight according to the first cone angle from the reference line to the first detection angle and the second weight according to the second cone angle from the reference line to the second detection element, by the determining function 447.

Figure 2:
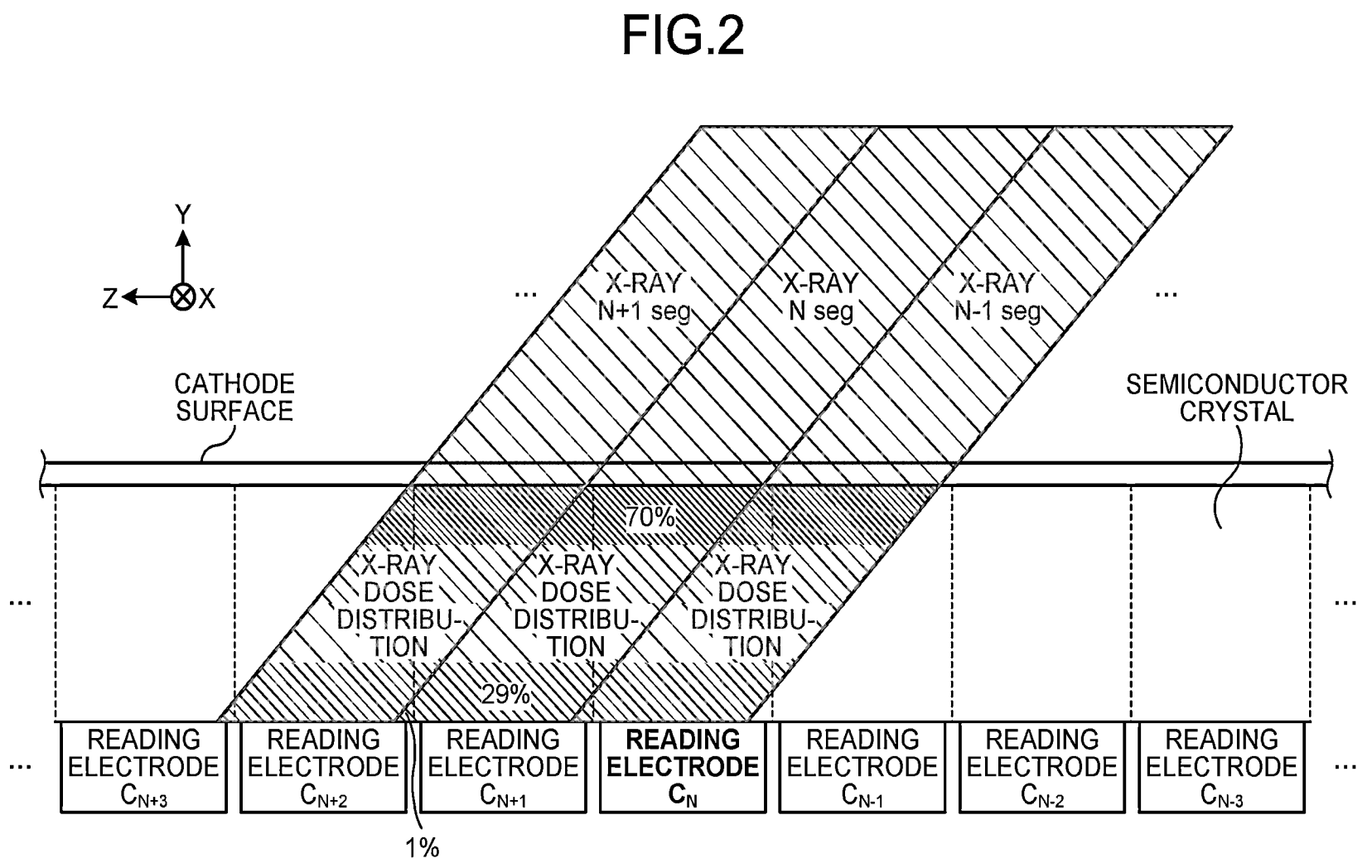

FIG. 2 is a diagram illustrating a portion of the X-ray detector 12 on an end portion side of the opening relative to the midplane together with an X-ray that obliquely enters the X-ray detector 12. More specifically, FIG. 2 illustrates a portion of the X-ray detector 12 close to an end portion of the opening on a + side in the Z-axis direction, that is, an end portion of the opening close to an end portion (foot portion of the subject P) on the + side in the Z-axis direction of the table top 33 illustrated in FIG. 1, together with an X-ray that obliquely enters the X-ray detector 12.

In FIG. 2, it is assumed that the first detection element is a reading electrode $C_N$. Moreover, in FIG. 2, a part $N_{seg}$ of X-ray generated in the X-ray tube 11 indicates an X-ray (hereinafter, denoted as obliquely incident X-ray) that obliquely enters the cathode surface (opposing surface) that is opposed to the reading electrode $C_N$ corresponding to the first detection element. In FIG. 2, a ratio of the first output that is output from the reading electrode $C_N$ with respect to all outputs from plural reading electrodes (reading electrode $C_N$, reading electrode $C_{N+1}$, reading electrode $C_{N+2}$) originated from an obliquely incident X-ray is indicated as 70%. In other words, 70% described above indicates a ratio at which the part $N_{seg}$ of X-ray is converted into an electric charge in the semiconductor crystal surrounded by dotted lines in a region right above the reading electrode $C_N$.

Moreover, in FIG. 2, a ratio of the second output that is output from the reading electrode $C_{N+1}$ to entire output from the reading electrodes (reading electrode $C_N$, reading electrode $C_{N+1}$, reading electrode $C_{N+2}$) originated in an obliquely incident X-ray is indicated as 29%. In other words, 29% described above indicates a ratio at which the part $N_{seg}$ of X-ray is converted into an electric charge in the semiconductor crystal surrounded by dotted lines in a region right above the reading electrode $C_{N+1}$.

Furthermore, in FIG. 2, a ratio of the second output that is output from the reading electrode $C_{N+2}$ to the entire output from the reading electrodes (reading electrode $C_N$, reading electrode $C_{N+1}$, reading electrode $C_{N+2}$) originated in an obliquely incident X-ray is indicated as 1%. In other words, 1% described above indicates a ratio at which the part $N_{seg}$ of X-ray is converted into an electric charge in the semiconductor crystal surrounded by dotted lines in a region right above the reading electrode $C_{N+2}$. In the example illustrated in FIG. 2, the second detection element corresponds to two electrodes, the reading electrode $C_{N+1}$ and the reading electrode $C_{N+2}$.

That is, when a geometry of a detection element as illustrated in FIG. 2 and oblique incidence of X-ray are assumed, 70% of the output from the electrode $C_N$, 29% of the output from the reading electrode $C_{N+1}$, and 1% of the output from the reading electrode $C_{N+2}$ contribute to an ideal output $C_{iN}$ of the first output. Specifically, in the example illustrated in FIG. 2, the ideal output $C_{iN}$ relating to the first detection element (reading electrode $C_N$) is calculated by following Equation (1).

$$C_{iN}=k_{N,N}\times C_N+k_{N,N+1}\times C_{N+1}+k_{N,N+2}\times C_{N+2} \tag{1}$$

In the right side of Equation (1), $C_N$ indicates an output (the first output) of the first detection element, that is, the reading electrode $C_N$. Moreover, in the right side of Equation (1), $C_{N+1}$ and $C_{N+2}$ indicate the second output of the second detection element (the reading electrode $C_{N+1}$ and the reading electrode $C_{N+2}$). Furthermore, in the right side of Equation (1), $k_{N,\ N}$ indicates the first weight, and $k_{N,\ N+1}$ and $k_{N,\ N+2}$ indicate the second weight. As illustrated in FIG. 2, the first weight $k_{N,\ N+1}$ is 0.7, and the second weight $k_{N,\ N+1}$, $k_{N,\ N+2}$ are 0.29, 0.01, respectively. Therefore, the processing circuitry 44 determines the ideal output $C_{iN}$ of the first detection element (the reading electrode $C_N$) by following Equation (2) by using the determining function 447.

$$C_{iN}=0.7\times C_N+0.29\times C_{N+1}+0.1\times C_{N+2} \tag{2}$$

Numeric values (0.7, 0.29, 0.01) of the first weight and the second weight in FIG. 2 and Equation (2) are one example, and they vary depending on an incident angle of an X-ray to the first detection element, that is, a column number. Generally, when the total number of detection elements along the column direction is n, and they are numbered from 1 to n along the cone angle direction (Z-axis direction), Equation (1) is generalized by Equation (3) below to be expressed.

$$\overrightarrow{C'_n} = \begin{pmatrix} k_{1,1} & \cdots & k_{1,n} \\ \vdots & \ddots & \vdots \\ k_{n,1} & \cdots & k_{n,n} \end{pmatrix} \times \overrightarrow{C_n} \tag{3}$$

A vector $\overrightarrow{C'_n}$ on the left side in above Equation (3) indicates an ideal output having plural ideal outputs respectively corresponding to the detection elements as components. Moreover, a vector $\overrightarrow{C_n}$ on the right side in above Equation (3) indicates a measured output vector having plural outputs (measured values) respectively corresponding to the detection elements as a vector component.

Furthermore, a matrix (hereinafter, denoted as weighting matrix) on the right side in above Equation (3)

$$\begin{pmatrix} k_{1,1} & \cdots & k_{1,n} \\ \vdots & \ddots & \vdots \\ k_{n,1} & \cdots & k_{n,n} \end{pmatrix}$$

expresses plural weights relating to the detection elements as a matrix. In other words, the weighting matrix corresponds to a coefficient matrix (for example, correlation matrix) indicating a correlation coefficient as a weight of each component in the measured output vector $\vec{C}_n$ indicating a measured value of output relating to the X-ray detector 12, and an ideal output vector $\vec{C'}_n$ indicating an ideal output relating to the X-ray detector 12. When the total number n of the detection elements along the column direction is an odd number, a detection number n/2+1 corresponds to the midplane. In this case, the weight $k_{n/2+1, i}$ (excluding $1 \leq i \leq n{:}n/2+1$) is all zero, and the weight $k_{n/2+1, n/2+1}$ is 1. Ideally, the coefficient matrix is a matrix that has symmetrical components about a diagonal line connecting the first row of the N-th column and the N-th row of the first column.

In the weighting matrix, qualitatively, for a detection element having a larger cone angle, the weight of an adjacent element in a direction of the larger cone angle than the detection element (and plural detection elements along an increasing direction including the adjacent element) increases, and the weight relating to an output of the detection element itself decreases. For example, in the diagonal components of the weighting matrix, the first weight decreases, as the number of rows and the number of columns increase and decrease from a weight $k_{n/2, n/2}$ corresponding to the midplane. Moreover, for example, in the non-diagonal components of the weighting matrix, the second weight relating to the second detection element along the large cone angle direction increases from the weight $k_{n/2, n/2}$ corresponding to the midplane, as the number of rows and the number of columns increase and decrease. In other words, in the weighting matrix, as the first angle increases, the first weight decreases and the second weight increases. The weight matrix generated by various kinds of simulation (for example, Monte Carlo simulation) or preliminary calibration test (experiment) is stored in the memory 41.

Although the cone angle direction is focused in the example expressed by FIG. 2 and the above equation, the fan angle direction may be focused instead of the cone angle direction. Moreover, for example, when an FPD is used as the X-ray detector 12, that is, when an incident angle of an X-ray is large in a channel in which the fan angle direction is large, a dimension of a matrix operation by the above equation may be extended. In this case, the measured output vector and the ideal output vector are to be, for example, a matrix indicating an output relating to the plural detection elements relating to the cone angle direction and the fan angle direction, and the weighting matrix is four tensors having the cone angle direction and the fan angle direction as parameters (indexes).

The above processing implemented by the determining function 447 may be implemented by the preprocessing function 442. In this case, the preprocessing function 442 performs processing by the determining function 447 with respect to data (for example, the number of counts) before subjected to the preprocessing, before performing the preprocessing. Moreover, the above processing implemented by the determining function 447 may be implemented by the DAS 18. In this case, the DAS 18 performs processing by the determining function 447 with respect to detection data (for example, pure raw data or raw data (the number of counts)).

The processing circuitry 44 outputs the ideal output determined for the respective detection elements by the determining function 447 to the preprocessing function 442. The determination of the ideal output by the determining function 447 corresponds to correction of an influence of oblique incidence of an X-ray with respect to the X-ray detector 12. That is, the ideal output corresponds to correction data in which an influence of oblique incidence of an X-ray with respect to the X-ray detector 12 has been corrected. The preprocessing function 442 performs preprocessing with respect to the correction data, to generate projection data (hereinafter, denoted as corrected projection data). The corrected projection data corresponds to projection data in which an influence of oblique incidence of an X-ray with respect to the X-ray detector 12 is reduced. The reconstruction processing function 443 generates a reconstruction image (hereinafter, denoted as corrected reconstruction image) by reconstruction processing with respect to the corrected projection data. That is, the processing circuitry 44 performs the reconstruction processing with respect to the projection data based on an output corresponding to a reconstruction position by using the reconstruction processing function 443, to generate a reconstruction image (corrected reconstruction image). The corrected reconstruction image is, for example, stored in the memory 41, and is displayed on the display 42 by the display control function 446. The corrected reconstruction image corresponds to a reconstruction image in which an influence of oblique incidence of an X-ray with respect to the X-ray detector 12 is corrected.

Figure 3:
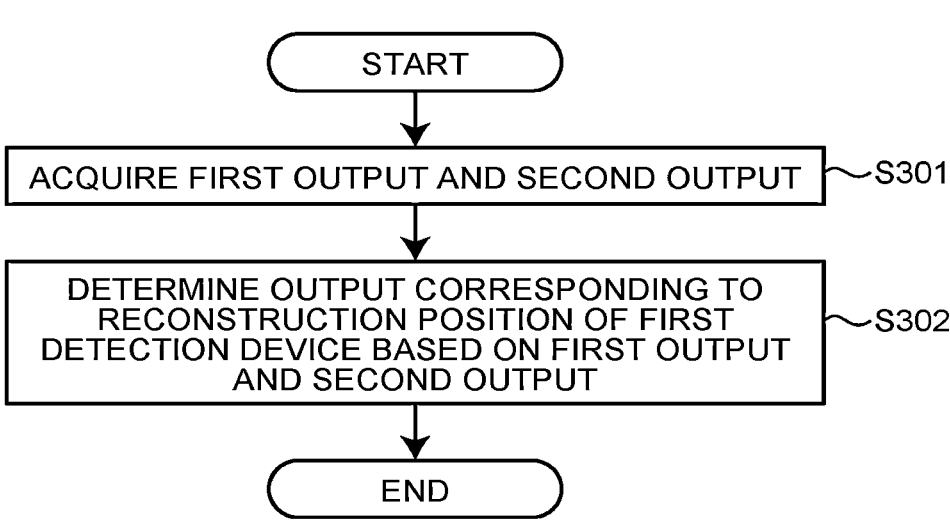
FIG. 3 is a flowchart illustrating an example of procedure of output determination processing according to the first embodiment.

As described above, the entire configuration of the PCCT apparatus 1 has been explained as one example of the radiation diagnostic apparatus. In the following, a procedure of the output determination processing will be explained by using FIG. 3. The output determination processing is to determine an output corresponding to a reconstruction position of the first detection element based on the collected first output and second output. FIG. 3 is a flowchart illustrating an example of the procedure of the output determination processing.

Output Determination Processing

Step S301

The data collecting circuitry 18 collects a first output of the first detection element that is included in the plural radiation detection elements aligned in a two-dimensional direction, and a second output of the second detection element around the first detection element, by scanning performed with respect to the subject P. Thus, the first output and the second output are acquired.

Step S302

The processing circuitry 44 determines an output corresponding to a reconstruction position of the first detection element based on the first output and the second output by using the determining function 447. Because the determination of an output corresponding to the reconstruction position is based on the above explanation, explanation thereof will be omitted.

The radiation diagnostic apparatus according to the first embodiment described above determines an output (for example, an ideal output of the first detection element) corresponding to a reconstruction position of the first detection element based on the first output relating to the first detection element included in the plural radiation detection elements that are aligned in a two-dimensional direction, and the second output relating to the second detection element around the first detection element. For example, the radiation diagnostic apparatus according to the present embodiment determines an output (for example, an ideal output) corresponding to a reconstruction position by using the first weight according to the first angle from the reference line to the first detection element and the second weight according to the second angle from the reference line to the second detection element in a direction within a plane including the first detection element and the second detection element out of the two-dimensional direction. Specifically, the radiation diagnostic apparatus according to the present embodiment determines an output (for example, an ideal output) corresponding to a reconstruction position by adding up the first multiplication value obtained by multiplying the first output by the first weight and the second multiplication value obtained by multiplying the second output by the second weight.

For example, the radiation diagnostic apparatus according to the first embodiment is an X-ray CT apparatus, the two-dimensional direction is the cone angle direction and the fan angle direction, radiation is an X-ray, the first detection element and the second detection element are arranged along the cone angle direction, and an output (for example, an ideal output) corresponding to a reconstruction position is determined by using the first weight according to the first cone angle from the reference line to the first detection element and the second weight according to the second cone angle from the reference line to the second detection element. In this case, in the radiation diagnostic apparatus according to the present embodiment, the first output, the second output, and the output (for example, an ideal output) corresponding to a reconstruction position may be the number of counts obtained by counting photons in the X-ray. The radiation diagnostic apparatus according to the present embodiment performs the reconstruction processing with respect to projection data based on the output (for example, an ideal output) corresponding to a reconstruction position, to generate a reconstruction image. Furthermore, in the radiation diagnostic apparatus according to the first embodiment, the first weight and the second weight are set based on a material to convert a radiation into electron or visible light in the first detection element and the second detection element, thickness of the material, and an angle (that is, an incident angle of an X-ray that obliquely enters the opposing surface) at which the radiation enters the first detection element, and as the first angle increases, the first weight decreases and the second weight increases.

From this fact, according to the radiation diagnostic apparatus according to the first embodiment, an influence on pure raw data or raw data caused by oblique incidence of an X-ray to an opposing surface originating in at least one of the cone angle and the fan angle can be corrected. Thus, according to the present radiation diagnostic apparatus, misalignment of detection position of a radiation originated in oblique incidence of an X-ray can be corrected, and projection data can be acquired at an original position corresponding to the detection position of an X-ray. For reasons described above, according to this radiation diagnostic apparatus, a medical image (X-ray image based on projection data or corrected reconstruction image) in which deterioration of the image quality, such as elongation of an image in a body axis direction of the subject P and/or a right-and-left direction, is reduced and space resolution is improved can be generated. Therefore, according to this radiation diagnostic apparatus, the quality of radiation examination with respect to the subject P can be improved.

Application

The PCCT apparatus 1 collects data (the number of counts) for each energy range (energy bin). Moreover, the semiconductor crystal of the X-ray detector 12 in the PCCT apparatus 1 has a small X-ray absorption area compared to ordinary integral-type X-ray detectors. Accordingly, the thickness of the X-ray detector 12 in the PCCT apparatus 1 is thick compared to ordinary integral-type X-ray detectors. For this reason, as energy of an X-ray becomes higher, an influence oblique incidence of the X-ray becomes larger. That is, in the conventional PCCT apparatus 1, a reconstruction image reconstructed for each energy bin is to be more elongated along a body axis direction of the subject P as the energy representing an energy bin becomes higher, that is, when it is a reconstruction image of a higher energy.

Therefore, the present application is to determine an ideal output for each of plural energy bins by using plural weighting matrixes corresponding to the plural energy bins. In the weighting matrixes, the contribution rate $k_{N, N}$ to the own detection element corresponding to the first weight decreases, and a contribution rate $k_{N, N'>N}$ corresponding to the second weight from the second detection element including an adjacent element to the first detection element in the X-ray detector 12 close to an end portion on a + side in the Z-axis direction increases. Moreover, in the weighting matrixes, a contribution rate $k_{N, N'<N}$ corresponding to the second weight from the second detection element including an adjacent element to the first detection element in the X-ray detector 12 close to an end portion on a − side in the Z-axis direction increases. In other words, the first weight in the respective energy bins decreases as the energy becomes higher in representative energies that represent the energy bins, and the second weight in the respective energy bins increase as the energy becomes higher in the representative energies.

The first output in the present application is, for example, plural first counts according to the energy bins in an X-ray. Moreover, the second output in the present application is, for example, plural second counts according to the energy bins in an X-ray. In this case, the processing circuitry 44 determines the number of counts as an output (for example, an ideal output) corresponding to a reconstruction position for each of the energy bins based on the first weight, the second weight, the first count, and the second count by using the determining function 447 for each of the energy bins.

Specifically, the processing circuitry 44 determines an output (for example, an ideal output) corresponding to a reconstruction position for each of the energy bins by using Equation (4) below by the determining function 447.

$$\overrightarrow{C'_{n,Ebin}} = \begin{pmatrix} k_{1,1} & \cdots & k_{1,n} \\ \vdots & \ddots & \vdots \\ k_{n,1} & \cdots & k_{n,n} \end{pmatrix}_{Ebin} \times \overrightarrow{C_{n,Ebin}} \tag{4}$$

A vector $\overrightarrow{C'_{n,Ebin}}$ on a left side in Equation (4) above indicates an ideal output vector for each energy bin including outputs (for example, ideal outputs) corresponding to reconstruction positions respectively corresponding to the detection elements as components. Moreover, a vector $\overrightarrow{C_{n,Ebin}}$ on a right side in Equation (4) above indicates a measured output vector for each energy bin including outputs (measured values) respectively corresponding to the detection elements as components of the vector.

Furthermore, a weighting matrix $$\begin{pmatrix} k_{1,1} & \cdots & k_{1,n} \\ \vdots & \ddots & \vdots \\ k_{n,1} & \cdots & k_{n,n} \end{pmatrix}_{Ebin}$$

of each energy on the right side in the Equation (4) above expresses weights relating to the detection elements as a matrix of each energy bin. The energy bins on both sides of Equation (4) all express the same energy bin. The weighting matrix of each energy bin corresponds to a coefficient matrix (for example, correlation matrix) indicating a correlation coefficient of respective components (outputs of respective detection elements) in a measured output vector of each energy bin $\overline{C_{n,Ebin}}$ and an ideal output vector of each energy bin $\overline{C'_{n,Ebin}}$ as a weight. Because other characteristics of the weighting matrix of each energy bin are same as the first embodiment, explanation thereof is omitted. Moreover, as for processing in the determining function 447 also, because processing similar to that of the first embodiment is repeated in each energy bin, explanation thereof is omitted.

In the radiation diagnostic apparatus according to the application of the first embodiment described above, the first output is the plural first counts according to plural energy bins in an X-ray, the second output is the plural second counts according to plural energy bins, and the number of counts is determined as an output (for example, an ideal output) corresponding to a reconstruction position for each of the energy bins based on the first weight, the second weight, the first count, and the second count for each of the energy bins. Moreover, in the radiation diagnostic apparatus according to the present application, the first weight in each of the energy bins decreases as the energy becomes higher in representative energies representing the energy bins, and the second weight in each of the energy bins increases as the energy in the representative energies becomes higher.

For the above reason, according to the radiation diagnostic apparatus according to the application of the first embodiment, because the contribution rate by an energy of an X-ray varies, the number of counts measured independently for each of energy bins can be corrected by using a weighting matrix (coefficient matrix) for each of the energy bins. According to the radiation diagnostic apparatus according to the present application, more accurate correction is possible for oblique incidence of an X-ray, and accuracy of correction of the number of counts can be further improved. moreover, because an X-ray sectional area is small in a semiconductor detector used as the X-ray detector 12 and influence of oblique incidence of an X-ray tends to be large, an effect of correction can be further increased by using the radiation diagnostic apparatus according to the present application.

In addition, according to the radiation diagnostic apparatus, a difference in influence of oblique incidence among energy bins when performing spectral imaging can be reduced by operation by the determining function 447, and an influence of oblique incidence of an X-ray can be accurately corrected also in counting imaging, which is addition of spectral imaging. That is, according to the radiation diagnostic apparatus according to the present application, a degree of misalignment of position, a degree of which varies according to an energy bin can be corrected for each of energy bins and, therefore, misalignment of position among the energy bins can be corrected, and an accurate spectral imaging is possible. From this fact, according to the radiation diagnostic apparatus according to the present application, space resolution in a body axis direction of a reconstruction image can be improved. Because other effects are same as those of the first embodiment, explanation thereof is omitted.

Modification

The present modification is characterized by the X-ray detector 12 configured with plural small modules including plural detection elements. That is, in the X-ray detector 12 of the present modification, a surface detector of a large area is constructed by arranging detectors of small module units, not by an integrated configuration in which plural detection elements are arranged in a two-dimensional direction. In this case, when arranging the small modules at designed positions, a gap is always generated between adjacent two small modules.

Figure 4:
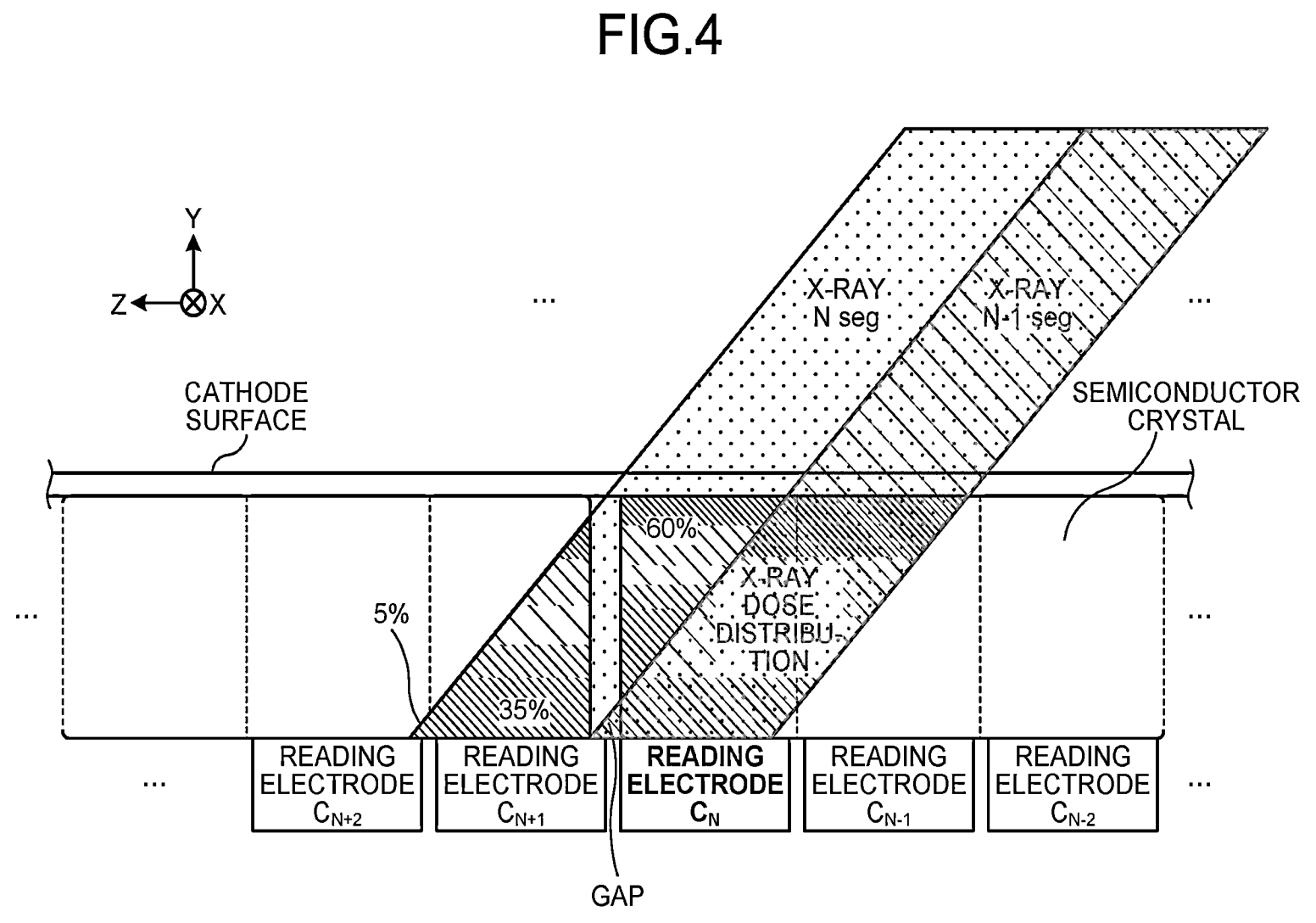

FIG. 4 is a diagram illustrating a portion of the X-ray detector 12 on an end portion side of an opening relative to a midplane together with an X-ray that obliquely enters the X-ray detector 12 according to the present modification. A difference between FIG. 2 and FIG. 4 is that a gap is present between the N-th reading electrode $C_N$ and the (N+1)-th reading electrode $C_{N+1}$. As illustrated in FIG. 4, an X-ray that has obliquely entered the gap obliquely enters detection elements around the reading electrode $C_N$ including adjacent elements. Respective components in a weighting matrix in the present modification are set considering the gap as illustrated in FIG. 4. That is, as illustrated in FIG. 4, when a gap is present between the first detection element and the second detection element corresponding to the reading electrode $C_N$, the first weight is set to be small compared to when the gap is not present, and the second weight is set to be large compare to when the gap is not present.

By these configurations, according to the present modification, the components (respective correction terms) in the weighting matrix in the first embodiment and the application of the first embodiment can be set considering the increase of oblique incidence of an X-ray caused by the gap, and interpolation of discontinuity of measured output caused by the gap between small modules in the X-ray detector 12 can be performed. That is, according to the present modification, by tiling the detection modules in a small module, weight setting enables calculation of an ideal output even in a region in which gaps between detection modules are not uniform to avoid interference, or a region in which an influence of oblique incidence of an X-ray to adjacent elements is large due to gaps between detection modules. Because other effects of the present modification are similar to those of the first embodiment and the application of the first embodiment, explanation thereof is omitted.

Second Embodiment

A difference from the first embodiment is that a radiation detector includes a processing circuitry performing the determining function 447. Hereinafter, for specific explanation, the radiation detector is assumed to be an X-ray detector mounted on a PCCT apparatus. In this case, the determining function 447 in the processing circuitry 44 is unnecessary in the PCCT apparatus 1 illustrated in FIG. 1.

Figure 5:
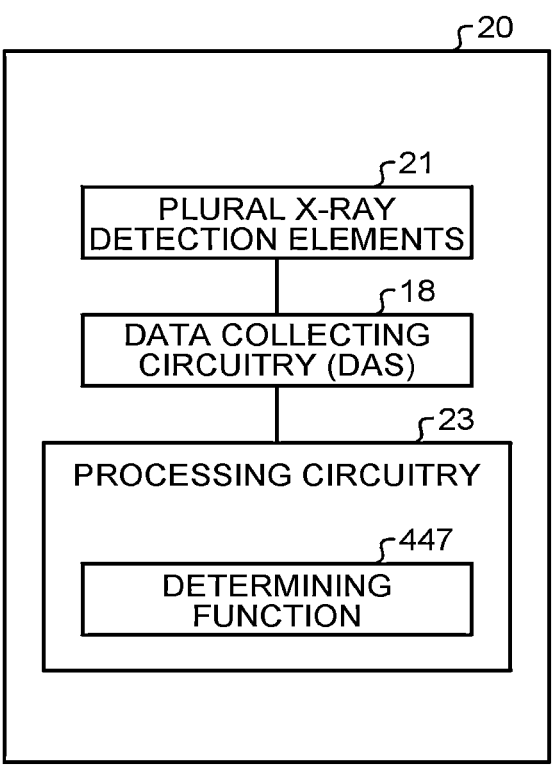
FIG. 5 is a diagram illustrating an example of a configuration of an X-ray detector corresponding to a radiation detector according to a second embodiment.

FIG. 5 is a diagram illustrating an example of a configuration of an X-ray detector 20 corresponding to a radiation detector in the present embodiment. As illustrated in FIG. 5, the X-ray detector 20 includes plural X-ray detection elements 21, the data collecting circuitry (DAS) 18, and a processing circuitry 23. As for the X-ray detection elements 21, the X-ray detection elements 21 arranged in a two-dimensional direction are similar to those of the first embodiment and, therefore, explanation thereof is omitted. The X-ray detection elements 21 correspond to, for example, plural radiation detection elements.

For example, the DAS 18 collects the first count based on an output from the first detection element included in the X-ray detection elements, and collects the second counts based on an output from the second detection element around the first detection element. Because a configuration and a function of the DAS 18 are similar to those of the first embodiment, explanation thereof is omitted.

The processing circuitry 23 is, for example, a processor, and reads respective programs from the memory 41, and implements functions corresponding to the read programs by executing the programs. Because a hardware configuration of the processing circuitry 23 is similar to that of the first embodiment, explanation thereof is omitted. The processing circuitry 23 determines an ideal count relating to the first detection element when it is supposed that a surface at which a radiation first arrives in the first detection element is an incident position of the radiation, based on the first count and the second count by using the determining function 447. Because specific processing performed by the determining function 447 is similar to that of the first embodiment, explanation thereof is omitted. Moreover, because a procedure of output determination processing in the present embodiment is similar to that of the first embodiment, explanation thereof is omitted.

As for an application and a modification of the second embodiment, the application and the modification of the first embodiment can be applied and, therefore, explanation is omitted. Moreover, because an effect of the second embodiment is also similar to that of the first embodiment, explanation is omitted.

When the technical idea of the present embodiment is implemented by the output determination method, in the output determination method, the first output relating to the first detection element that is included in the radiation detection elements arranged in a two-dimensional direction, and a second output relating to the second detection element around the first detection element are collected, and an output corresponding to a reconstruction position of the first detection element is determined based on the first output and the second output. Because a procedure and an effect of this output determination method are similar to those of the first embodiment, explanation thereof is omitted.

When the technical idea of the present embodiment is implemented by an output determination program, the output determination program causes a computer to implement collecting the first output relating to the first detection element that is included in the radiation detection elements arranged in a two-dimensional direction, and a second output relating to the second detection element around the first detection element, and determining an output corresponding to a reconstruction position of the first detection element based on the first output and the second output. In this case, the program that causes to execute the method can also be stored in a recording medium, such as a magnetic disk (hard disk, and the like), an optical disk (CD-ROM, DVD, and the like), and a semiconductor memory, to be distributed. Because a procedure and an effect of this output determination program are similar to those of the first embodiment, explanation thereof is omitted.

According to at least one of the embodiments and the like explained above, an influence of oblique incidence of radiation to a radiation detector can be reduced.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

Note 1

A radiation detector including:

plural radiation detection elements that are arranged in a two-dimensional direction; and a determining unit that determines, based on a first output relating to a first detection element included in the radiation detection elements, and a second output relating to a second detection element, an output corresponding to a reconstruction position of the first detection element.

Note 2

The determining unit may determine the output corresponding to the reconstruction position by using a first weight according to a first angle from a reference line to the first detection element in a direction in a plane including the first detection element and the second detection element out of the two-dimensional direction, and a second weight according to a second angle from the reference line to the second detection element, wherein a second weight may be provided for each second detection element of the at least one second detection elements.

Note 3

The determining unit may determine the output corresponding to the reconstruction position by adding up a first multiplication value obtained by multiplying the first output by the first weight and a second multiplication value obtained by multiplying the second output by the second weight.

Note 4

The radiation detector is mounted on an X-ray computed tomography apparatus, the two-dimensional direction is a cone angle direction and a fan angle direction, the radiation is an X-ray, the first detection element and the second detection element are arranged along the cone angle direction, and the determining unit may determine the output corresponding to the reconstruction position by using the first weight according to a first cone angle from the reference line to the first detection element, and the second weight according to a second cone angle from the reference line to the second detection element.

Note 5

The first output, the second output, and the output corresponding to the reconstruction position may be the number of counts obtained by counting photons in the X-ray.

Note 6

The first output is plural first counts according to plural energy bins in the X-ray, the second output is plural second counts according to the energy bins, and the determining unit may determine the number of counts as the output corresponding to the reconstruction position of each of the energy bin based on the first weight, the second weight, the first count, and the second count for each of the energy bins.

Note 7

The first weight in each of the energy bins may decrease as an energy of plural representative energies representing the energy bins becomes higher, and the second weight in each of the energy bins may increase as the energy of the representative energies becomes higher.

Note 8

The first weight and the second weight are set based on a material that converts the radiation into electron or visible light in the first detection element and the second detection element, thickness of the material, and a first angle at which the radiation enters the first detection element, and as the first angle increases, the first weight may decrease and the second weight may increase.

Note 9

When a gap is present between the first detection element and the second detection element, the first weight may be set to be small compared to when the gap is not present, and the second weight may set to be large compared to when the gap is not present.

Note 10

An X-ray computed tomography apparatus equipped with the radiation detector according to any one of Notes 1 to 10, including a reconstruction processing unit that performs reconstruction processing with respect to projection data based on the output corresponding to the reconstruction position, to generate a reconstruction image.

Note 11

The reconstruction position may be a position that is used for calculation of reconstruction based on the output, and that indicates a representative point of the first detection element.

Note 12

A data collecting circuitry that collects the first count based on an output from the first detection element included in the radiation detection elements, and that collects the second count based on an output of the second detection element around the first detection element is further included, and the determining unit may determine the number of counts corresponding to reconstruction of the first detection element based on the first count and the second count.

Note 13

An X-ray computed tomography apparatus including the radiation detector according to any one of Notes 1 to 12.

Note 14

An output determination method including collecting a first output relating to a first detection element included in plural radiation detection elements that are arranged in a two-dimensional direction, and a second output relating to a second detection element; and determining an output corresponding to a reconstruction position of the first detection element based on the first output and the second output.

Note 15

A computer-readable non-volatile storage medium storing an output determination program that causes a computer to implement collecting a first output relating to a first detection element included in plural radiation detection elements that are arranged in a two-dimensional direction, and a second output relating to a second detection element; and determining an output corresponding to a reconstruction position of the first detection element based on the first output and the second output.

What is claimed is:

1. A radiation diagnostic apparatus, comprising:

a plurality of radiation detection elements that are arranged in a two-dimensional direction; and processing circuitry configured to determine, based on a first output of a first detection element included in the radiation detection elements, and a second output relating to a second detection element of at least one second detection element, an output corresponding to a reconstruction position of the first detection element, wherein the determined output is an output from the first detection element that occurs when the radiation incident on the reconstruction position of the first detection element is entirely converted into charge at the reconstruction position, wherein the processing circuitry is further configured to determine the output corresponding to the reconstruction position by using a first weight determined according to a first angle from a reference line to the first detection element in a direction in a plane including the first detection element and the second detection element out of the two-dimensional direction, and a second weight determined according to a second angle from the reference line to the second detection element, wherein a second weight is provided for each detection element of the at least one second detection element, and wherein the first weight and the second weight are set based on a material that converts the radiation into any one of electron and visible light in the first detection element and the second detection element, a thickness of the material, and a first angle at which the radiation enters the first detection element, and as the first angle increases, the first weight decreases and the second weight increases.

2. The radiation diagnostic apparatus according to claim 1, wherein the processing circuitry is further configured to determine the output corresponding to the reconstruction position by adding up a first multiplication value obtained by multiplying the first output by the first weight and a second multiplication value obtained by multiplying the second output by the second weight.

3. The radiation diagnostic apparatus according to claim 1, wherein the radiation diagnostic apparatus is an X-ray computed tomography apparatus, the two-dimensional direction is a cone angle direction and a fan angle direction, the radiation is an X-ray, the first detection element and the second detection element are arranged along the cone angle direction, and the processing circuitry is further configured to determine the output corresponding to the reconstruction position by using the first weight determined according to a first cone angle from the reference line to the first detection element, and the second weight determined according to a second cone angle from the reference line to the second detection element.

4. The radiation diagnostic apparatus according to claim 3, wherein the first output, the second output, and the output corresponding to the reconstruction position are a number of counts obtained by counting photons in the X-ray.

5. The radiation diagnostic apparatus according to claim 4, wherein the first output is a plurality of first counts according to a plurality of energy bins in the X-ray, the second output is a plurality of second counts according to the energy bins, and the processing circuitry is further configured to determine the number of counts as the output corresponding to the reconstruction position of each of the energy bins based on the first weight, the second weight, the first count, and the second count for each of the energy bins.

6. The radiation diagnostic apparatus according to claim 5, wherein the first weight in each of the energy bins decreases as an energy in a plurality of representative energies representing the energy bins becomes higher, and the second weight in each of the energy bins increases as the energy of the representative energies becomes higher.

7. The radiation diagnostic apparatus according to claim 1, wherein when a gap is present between the first detection element and the second detection element, the first weight is set to be small compared to when the gap is not present, and the second weight is set to be large compared to when the gap is not present.

8. The radiation diagnostic apparatus according to claim 1, wherein the processing circuitry is further configured to perform reconstruction processing with respect to projection data based on the output corresponding to the reconstruction position, to generate a reconstruction image.

9. The radiation diagnostic apparatus according to claim 1, wherein the reconstruction position is a position that is used by the processing circuitry to perform reconstruction based on the output, and that indicates a representative point of the first detection element.

10. A radiation detector, comprising:

a plurality of radiation detection elements that are arranged in a two-dimensional direction;

data collecting circuitry configured to collect a first count based on an output from a first detection element included in the radiation detection elements, and collect a second count based on an output from a second detection element of at least one second detection element; and processing circuitry configured to determine a number of counts corresponding to a reconstruction position of the first detection element based on the first count and the second count, wherein the number of counts is a number of counts output from the first detection element that occurs when the radiation incident on the reconstruction position of the first detection element is entirely converted into charge at the reconstruction position, wherein the processing circuitry is further configured to determine the output corresponding to the reconstruction position by using a first weight determined according to a first angle from a reference line to the first detection element in a direction in a plane including the first detection element and the second detection element out of the two-dimensional direction, and a second weight determined according to a second angle from the reference line to the second detection element, wherein a second weight is provided for each detection element of the at least one second detection element, and wherein the first weight and the second weight are set based on a material that converts the radiation into any one of electron and visible light in the first detection element and the second detection element, a thickness of the material, and a first angle at which the radiation enters the first detection element, and as the first angle increases, the first weight decreases and the second weight increases.

11. An output determination method, comprising:

collecting a first output relating to a first detection element included in a plurality of radiation detection elements that are arranged in a two-dimensional direction, and a second output relating to a second detection element of at least one second detection element; and determining an output corresponding to a reconstruction position of the first detection element based on the first output and the second output, wherein the determined output is an output from the first detection element that occurs when the radiation incident on the reconstruction position of the first detection element is entirely converted into charge at the reconstruction position, wherein the method further comprises determining the output corresponding to the reconstruction position by using a first weight determined according to a first angle from a reference line to the first detection element in a direction in a plane including the first detection element and the second detection element out of the two-dimensional direction, and a second weight determined according to a second angle from the reference line to the second detection element, wherein a second weight is provided for each detection element of the at least one second detection element, and wherein the first weight and the second weight are set based on a material that converts the radiation into any one of electron and visible light in the first detection element and the second detection element, a thickness of the material, and a first angle at which the radiation enters the first detection element, and as the first angle increases the first weight decreases and the second weight increases.

* * * * *